US012723604B2

(12) United States Patent
Oakley et al.

(10) Patent No.: US 12,723,604 B2
(45) Date of Patent: Sep. 1, 2026

(54) SWITCHING UNIT AND PNEUMATIC SYSTEM

(71) Applicant: Berlin Heart GmbH, Berlin (DE)

(72) Inventors: Matthew Oakley, Warendorf (DE); Thomas Reitinger, Cham (DE)

(73) Assignee: Berlin Heart GmbH, Berlin (DE)

( * ) Notice: Subject to any disclaimer, the term of this patent is extended or adjusted under 35 U.S.C. 154(b) by 441 days.

(21) Appl. No.: 17/296,889

(22) PCT Filed: Nov. 27, 2019

(86) PCT No.: PCT/EP2019/082714
§ 371 (c)(1),
(2) Date: May 25, 2021

(87) PCT Pub. No.: WO2020/109374
PCT Pub. Date: Jun. 4, 2020

(65) Prior Publication Data

US 2022/0049721 A1 Feb. 17, 2022

(30) Foreign Application Priority Data

Nov. 27, 2018 (EP) .................................... 18208490

(51) Int. Cl.
*F15B 13/06* (2006.01)
*A61M 60/435* (2021.01)

(52) U.S. Cl.
CPC ........... *F15B 13/06* (2013.01); *A61M 60/435* (2021.01); *F15B 2211/8757* (2013.01)

(58) Field of Classification Search
None
See application file for complete search history.

(56) References Cited

U.S. PATENT DOCUMENTS 3,791,775 A 2/1974 Bochnak et al.
4,162,543 A * 7/1979 Shumakov .......... A61M 60/196 623/3.28

(Continued)

FOREIGN PATENT DOCUMENTS

DE 3323862 A1 1/1985
EP 2 896 840 A1 7/2015

(Continued)

OTHER PUBLICATIONS

"Humphrey Valve Catalog" by Humphrey Products Company (Year: 2012).*

(Continued)

*Primary Examiner* — Michael Quandt
(74) *Attorney, Agent, or Firm* — Crowell & Moring LLP

(57) ABSTRACT

A switching unit connects a first pneumatic unit and a second pneumatic unit of a pneumatic system. The switching unit includes a channel structure; a first and a second inlet for introducing a pressure into the channel structure; a first and a second outlet for discharging the pressure; and a first and a second valve. The first inlet can be brought into a pressure-exchange connection to the first outlet via a first channel in a first switch position of the first valve or to the second outlet via a second channel in a second switch position of the first valve. The second inlet can be brought into a pressure-exchange connection to the first outlet via a third channel in a first switch position of the second valve or to the second outlet via a fourth channel in a second switch position of the second valve.

12 Claims, 3 Drawing Sheets

(56) References Cited

U.S. PATENT DOCUMENTS 4,516,567 A * 5/1985 Veragen ................ A61M 60/88 623/3.28
4,559,648 A * 12/1985 Affeld ................ A61M 60/122 623/3.28
4,611,578 A * 9/1986 Heimes ............... A61M 60/554 417/19
4,687,424 A * 8/1987 Heimes ............... A61M 60/531 417/384
6,126,403 A * 10/2000 Yamada .............. F04B 43/0081 417/46
6,807,981 B2 * 10/2004 Miyazoe ............. F16K 31/0634 137/884
7,637,440 B2 * 12/2009 Fukano ................... F16K 23/00 239/104
7,721,760 B2 * 5/2010 Hettinger ................ F16K 11/22 137/884
9,829,248 B2 * 11/2017 Folchert ................ F15B 21/048
10,088,062 B2 * 10/2018 Hering .................. A61M 60/43
10,927,865 B2 * 2/2021 Neef ................... F15B 13/0401
2018/0302026 A1 * 10/2018 Basel ...................... F15B 15/10

FOREIGN PATENT DOCUMENTS

GB 263866 A1 9/1927
JP S61253068 A * 11/1986

OTHER PUBLICATIONS

JP-S61253068-A machine translation to English from espacenet (Year: 2024).*

International Search Report for Application No. PCT/EP2019/082714, dated Feb. 3, 2020, European Patent Office, Rijswijk, Netherlands, pp. 1-4.

* cited by examiner

SWITCHING UNIT AND PNEUMATIC SYSTEM

CROSS-REFERENCE TO RELATED APPLICATIONS

This application is a 371 nationalization of international patent application PCT/EP2019/082714 filed Nov. 27, 2019, which claims priority under 35 USC § 119 to European patent application 18208490.5 filed Nov. 27, 2018. The entire contents of each of the above-identified applications are hereby incorporated by reference.

DETAILED DESCRIPTION

Figure 1:
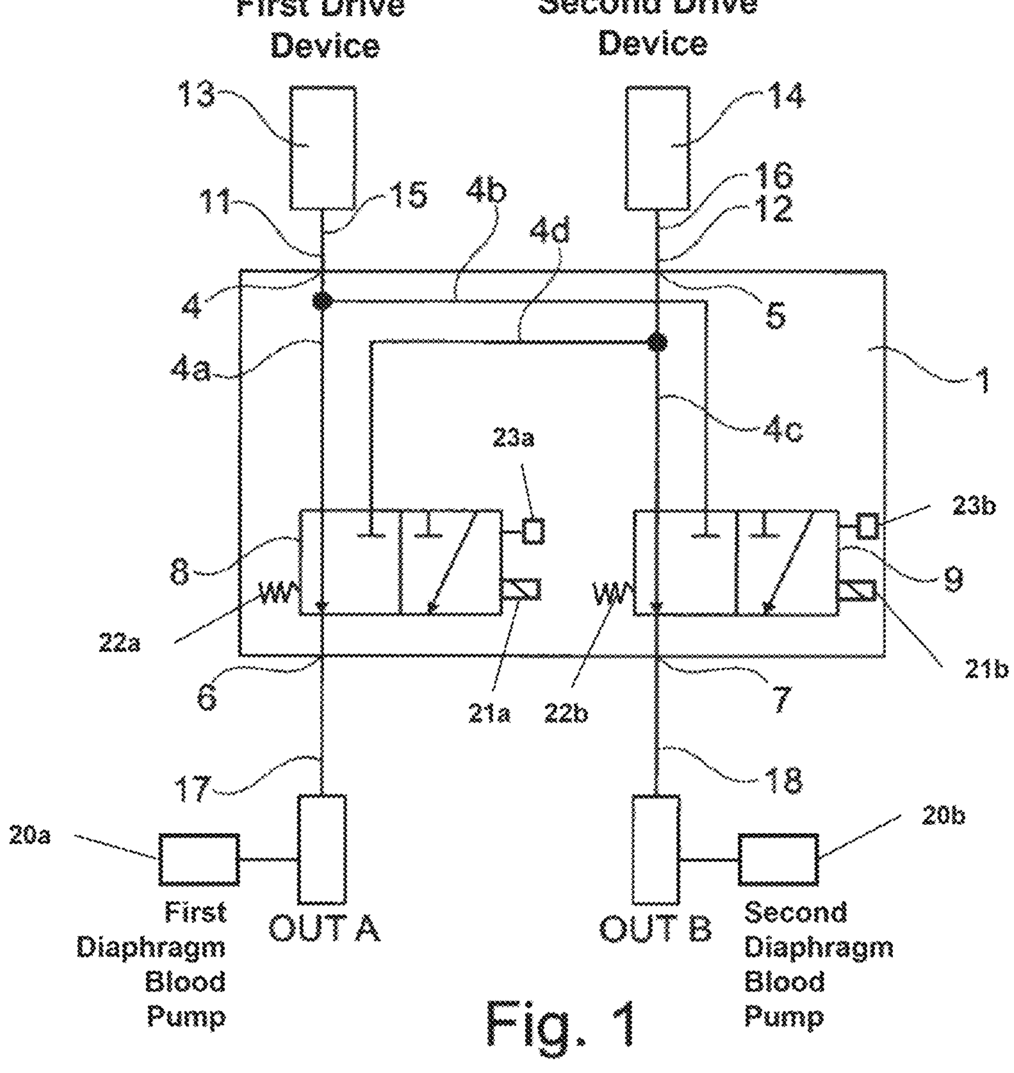
FIG. 1 shows a pneumatic circuit diagram of a pneumatic system according to the invention.

The present invention relates to a switching unit for interconnecting two pneumatic units. Furthermore, the invention relates to a pneumatic system comprising a switching unit of this kind and to a method for operating the pneumatic system.

For example, switching units (also referred to as switchover units (SOE)) in pneumatic blood pump drives are known. The function of the switching unit is to still ensure the operation of the pneumatic system in the event that a drive unit (EPE) fails. In the event of the failure of a pneumatic drive unit, the air path that is necessary to drive one or two blood pumps is connected by means of the switching unit such that, in the event of univentricular use, the airflow of the second drive unit is conducted to the one blood pump that is in use, and, in the event of biventricular use, the airflow of the remaining intact drive unit is conducted in alternation to the two blood pumps so that in both cases the patient's blood may still be pumped until the defective drive unit is exchanged.

A rotary piston valve is used in the switching unit known in the prior art. By rotating the valve piston of the rotary piston valve, different flow channel combinations may be provided. Due to the selective redirection of the airflow, in the biventricular assist mode both blood pumps may be controlled in alternation in the event of the failure of an EPE, and in the case of univentricular assistance it is possible to alter the air path such that a second drive unit located in the system may take over the supply of the blood pump.

Document DE 3323862 A1 describes a safety drive for an artificial heart. To increase the reliability of a drive for an artificial heart, in the event that the right drive should fail, this right drive may merely be shut down. In the event that the left drive should fail, however, the right drive, which is still in operation, may be connected to the left blood pump and thus constitutes a replacement drive within the drive itself.

The object of the present invention is to provide an alternative switching unit which has a compact design and, on a sustained basis, allows short switching cycles with a low pressure loss. A further object of the invention relates to a pneumatic system comprising a switching unit of this kind and to a method for operating the pneumatic system.

A switching unit according to the invention for interconnecting a first pneumatic unit and a second pneumatic unit of a pneumatic system comprises a main body with a channel structure extending through the main body, a first and a second inlet for introducing a pressure into the channel structure, a first and a second outlet for discharging at least some of the pressure from the channel structure, and also a first and a second valve.

Here, the first inlet may be brought via a first channel into a pressure exchange connection with the first outlet by setting a first switched position of the first valve or may be brought via a second channel into a pressure exchange connection with the second outlet by setting a second switched position of the first valve. This means that a pressure exchange connection is producible between the first inlet and the first outlet via the first channel by setting a first switched position of the first valve or between the first inlet and the second outlet via the second channel by setting a second switched position of the first valve.

The second inlet may be brought via a third channel into a pressure exchange connection with the first outlet by setting a first switched position of the second valve or may be brought via a fourth channel into a pressure exchange connection with the second outlet by setting a second switched position of the second valve. This means that a pressure exchange connection is producible between the second inlet and the first outlet via the third channel by setting a first switched position of the second valve or between the second inlet and the second outlet via the fourth channel by setting a second switched position of the second valve.

Here, a channel structure is not necessarily understood to mean continuous or open channels from an inlet to an outlet. At least part of the channel structure is closed by the setting of the first or second switched position of the valves. Depending on the switched position of the first valve, the first channel may be open, that is to say permeable for a pressure exchange, and the second channel may be closed, that is to say not permeable for a pressure exchange, or vice versa.

Similarly, depending on the switched position of the second valve, the third channel may be open and the fourth channel closed, or vice versa.

A pressure exchange connection between an inlet and an outlet is understood here to mean a connection between the inlet and the outlet which allows pressure to be exchanged between the inlet and the outlet. In particular, the pressure exchange connection may comprise a fluid connection.

Instead of a single rotary piston valve, the switching unit according to the invention thus has two independent valves, which may be combined with one another such that a desired 4/2-way function is provided. The use of two independent valves allows short switching times and leads to little wear in the switching unit.

The first and/or the second valve may preferably be a 3/2-way valve. If both the first and the second valve are 3/2-way valves, the combination of both valves in the switching unit thus provides a 4/2-way function.

In an advantageous embodiment of the invention, the first and/or the second valve may be formed as a piston valve with a valve piston, the valve piston being movable within the channel structure in linear fashion between the first and the second switched position.

The piston valve may also comprise a solenoid, the valve piston being movable by way of an interaction with the solenoid. In particular, the valve piston may be movable from the first switched position into the second switched position by switching on an electric current.

The piston valve may also have a return spring, by means of which the valve piston may be movable from the second switched position into the first switched position and/or may be held in the first switched position if there is no current switched on in the solenoid.

In a further embodiment of the invention, the first and/or the second valve may comprise a sensor, in particular a Hall sensor and/or an encoder, for measuring a piston position of the valve piston of the first and/or second valve. In particular, the Hall sensor may be designed to detect whether the valve piston of the first or second valve is in the first or second switched position.

The main body of the switching unit may preferably comprise or consist of a metal, in particular aluminum.

The invention also includes a pneumatic system, which comprises a first and a second pneumatic unit as well as a switching unit as described above, wherein the first pneumatic unit has a first diaphragm fluid pump and a first drive device, and wherein the second pneumatic unit has a second diaphragm fluid pump and a second drive device, and wherein the first and/or the second drive device are designed to drive the first and/or the second diaphragm fluid pump.

In particular, the first drive device may be connected via a first inlet pressure line to the first inlet of the switching unit, the first diaphragm fluid pump may be connected via a first outlet pressure line to the first outlet of the switching unit, the second drive device may be connected via a second inlet pressure line to the second inlet of the switching unit, and the second diaphragm fluid pump may be connected via a second outlet pressure line to the second outlet of the switching unit.

The first and/or the second drive device may be, for example, a piston pump or a compressor pump.

The invention also includes a method for operating a pneumatic system as described above. In particular, the method may comprise the fact that a switched position of the first or second valve is altered in order to change to another drive device for the first or second diaphragm fluid pump.

Furthermore, the method may comprise the fact that the valve piston of the first valve is in the first switched position and/or the valve piston of the second valve is in the second switched position, so that the first diaphragm fluid pump is driven by the first drive device and/or the second diaphragm fluid pump is driven by the second drive device.

Furthermore, the method may comprise the fact that the valve piston of the first valve is brought into the second switched position and/or the valve piston of the second valve is brought into the first switched position, so that the second diaphragm fluid pump is driven by the first drive device and/or the first diaphragm fluid pump is driven by the second drive device.

The switching unit according to the invention allows a low pressure loss in the event of a low working pressure of the drive devices. Furthermore, the switching unit is robust with respect to ambient influences, such as air humidity or oil-water emulsion. An additional filtering of the working air, which would otherwise result in an excessively high pressure loss, may thus be omitted.

An exemplary embodiment of a switching unit according to the invention and of a pneumatic system according to the invention will be described in greater detail hereinafter with reference to drawings. Different elements that are essential to the invention or also refine the invention advantageously will be referred to within the scope of a specific example, although some of these elements may also be used individually to refine the invention—also removed from the context of the example and further features of the example. Furthermore, like or similar reference signs are used in the drawings for like or similar elements, and their explanation has therefore been omitted to some extent.

FIG. 1 shows a pneumatic circuit diagram of a pneumatic system according to the invention. The pneumatic system comprises a switching unit 1 and also a first unit 11 and second pneumatic unit 12 connected pneumatically to the switching unit 1. The first pneumatic unit 11 comprises a first drive device 13. The first drive device 13 is pneumatically connected via a first inlet pressure line 15 to a first inlet 4 of the switching unit 1. Furthermore, the pneumatic system comprises a first diaphragm blood pump 20*a*, which is pneumatically connected via a first outlet pressure line 17 to a first outlet 6 of the switching unit 1. The second pneumatic unit 12 comprises a second drive device 14. The second drive device 14 is pneumatically connected via a second inlet pressure line 16 to a second inlet 5 of the switching unit 1. Furthermore, the pneumatic system comprises a second diaphragm blood pump 20*b*, which is pneumatically connected via a second outlet pressure line 18 to a second outlet 7 of the switching unit 1.

The drive devices 13 and 14 are designed to generate a predetermined pressure curve over time to drive the diaphragm fluid pumps. This pressure curve generated by the drive devices 13 and 14 is transferred via the inlet lines 15 and 16, the switching unit 1, and also the outlet pressure lines 17 and 18 to the diaphragm fluid pumps.

The switching unit 1 comprises a channel structure 3 (see FIG. 2) and also a first valve 8 and a second valve 9, wherein the first valve 8 and the second valve 9 are 3/2-way valves each with three ports and two switched positions. The first and the second valve 8, 9 allow each diaphragm blood pump to switch over between the first drive device 13 and the second drive device 14. In a first switched position of the first valve 8, which is shown in FIG. 1, the first inlet 4 and therefore the first drive device 13 are connected via a pressure line 4*a* to the first outlet 6 and the first diaphragm blood pump for an exchange of pressure. The pressure line 4*a* thus corresponds to a first channel within the channel structure 3 of the switching unit 1. In a second switched position of the first valve 8, which is not shown in FIG. 1, the first inlet 4 and therefore the first drive device 13 are connected via a pressure line 4*d* to the second outlet 7 and the second diaphragm blood pump for an exchange of pressure. The pressure line 4*b* thus corresponds to a second channel within the channel structure 3 of the switching unit 1. In a first switched position of the second valve 9, which is shown in FIG. 1, the second inlet 5 and therefore the second drive device 14 are connected via a pressure line 4*c* to the second outlet 7 and the second diaphragm blood pump for an exchange of pressure. The pressure line 4*c* thus corresponds to a third channel within the channel structure 3 of the switching unit 1. In a second switched position of the second valve 9, which is not shown in FIG. 1, the second inlet 5 and therefore the first drive device 14 are connected via a pressure line 4*d* to the second outlet 7 and the second diaphragm blood pump for an exchange of pressure. The pressure line 4*d* thus corresponds to a fourth channel within the channel structure 3 of the switching unit 1.

Operation of the pneumatic system is possible with different combinations of the switched positions of the first valve 8 and second valve 9. A first combination provides that the first valve 8 and the second valve 9 are both in the first switched position, wherein the pressure lines 4*a* and 4*c* are open and the pressure lines 4*b* and 4*d* are closed. In this case, the first diaphragm blood pump is driven by the first drive device 13 and the second diaphragm blood pump is driven by the second drive device 14. A second combination provides that the first and second valve 8 and 9 are both in the second switched position, wherein the pressure lines 4b and 4d are open and the pressure lines 4a and 4c are closed. In this case, the first diaphragm blood pump is driven by the second drive device 14 and the second diaphragm blood pump is driven by the first drive device 13. A third combination provides that the first valve 8 is in the first switched position and the second valve 9 is in the second switched position, wherein the pressure lines 4a and 4b are open and the pressure lines 4c and 4d are closed. In this case, the first drive device 13 drives both diaphragm blood pumps, whilst the second drive device 14 is not in operation. This combination is thus advantageous if the second drive device 14 fails, since biventricular operation of the pneumatic system may be maintained solely with the first drive device 13. A fourth combination provides that the first valve 8 is in the second switched position and the second valve is in the first switched position, wherein the pressure lines 4a and 4b are closed and the pressure lines 4c and 4d are open. In this case, the second drive device 14 drives both diaphragm blood pumps, whilst the first drive device 13 is not in operation. This combination is thus advantageous if the first drive device 13 fails, since biventricular operation of the pneumatic system may be maintained solely with the second drive device 14.

Figure 2:
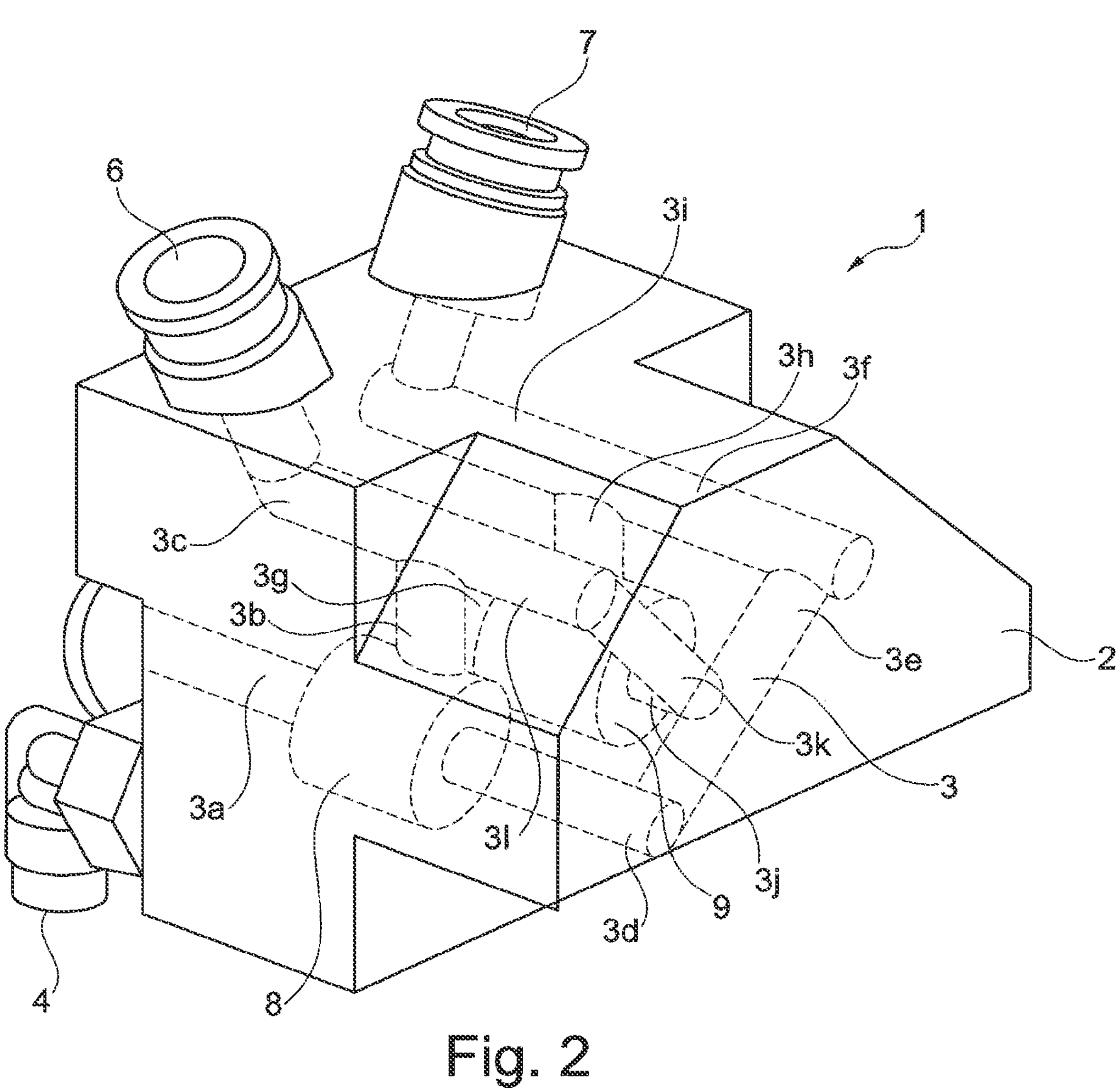
FIG. 2 shows a perspective view of a switching unit according to the invention.
Figure 3:
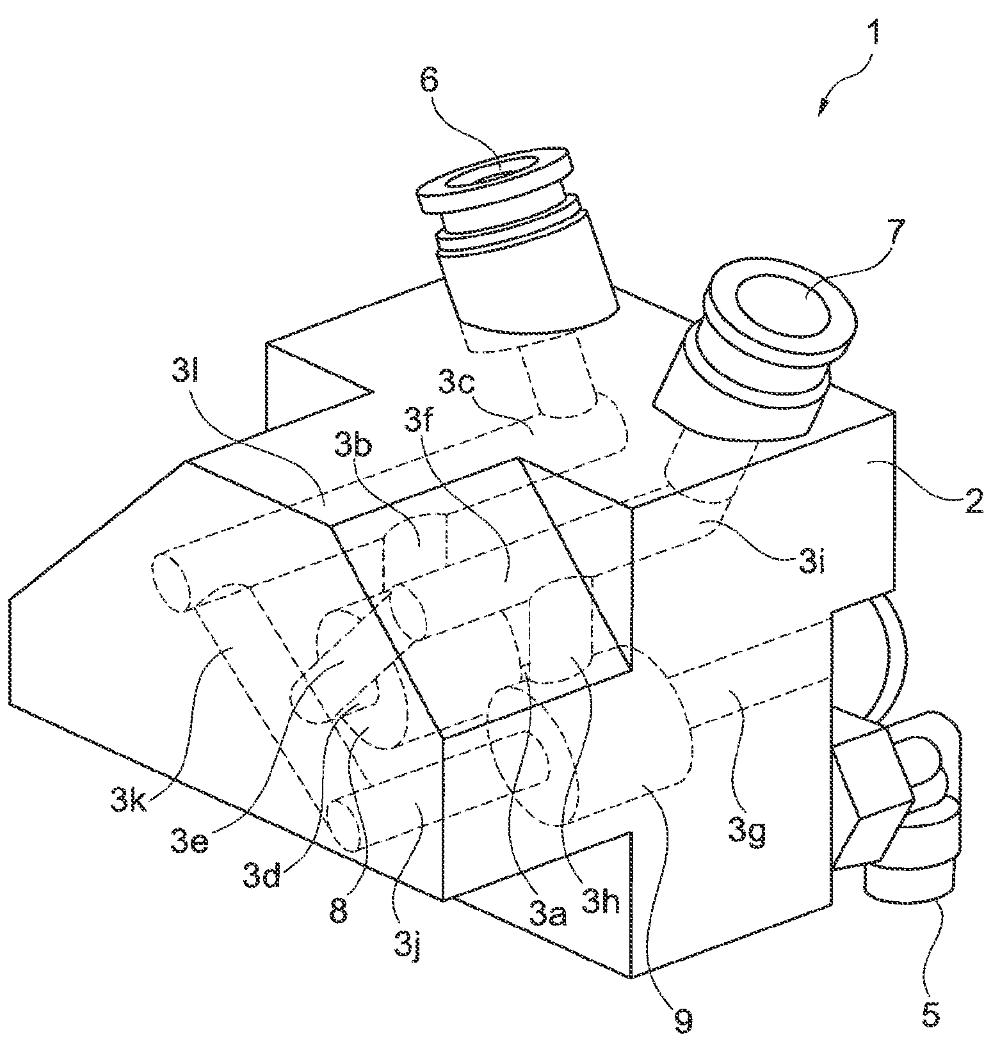
FIG. 3 shows a further perspective view of the switching unit according to the invention.

FIGS. 2 and 3 show perspective views of an exemplary embodiment of a switching unit 1 according to the invention from the front left and front right. The switching unit 1 has a substantially cuboid-shaped main body 2 with a channel structure 3 running inside the main body 2. Two ports protrude from the main body 2 on a rear side of the main body 2 for a first inlet pressure line and a second inlet pressure line and form a first inlet 4 and a second inlet 5. Two further ports for outlet pressure lines protrude from the main body on a top side of the main body 2 adjacently to the rear side of the main body 2. These ports form a first and a second outlet 6 and 7. The channel structure 3 is able to transfer a pressure present at an inlet 4, 5 to an outlet 6, 7. Furthermore, the first and the second valves 8 and 9 are located inside the main body 2. The channel structure 3 has a plurality of channel portions 3a to 31, which may be combined with the aid of the valves 8 and 9 such that pressure exchange connections between at least one of the inlets 4, 5 and the outlets 6 and 7 are made possible.

As described for FIG. 1, four different combinations of the switched positions of the first and second valve 8 and 9 are conceivable. In the first combination the pressure lines 4a and 4c in FIG. 1 are open. The pressure lines 4a and 4c correspond to a first channel and a second channel, wherein the first channel is composed substantially of channel portions 3a, 3b and 3c and the second channel is composed substantially of channel portions 3g, 3 h and 3i. The channel portions 3a and 3i, 3b and 3h, and also 3c and 3g run parallel to one another. In the second combination the pressure lines 4b and 4d in FIG. 1 are open. The pressure lines 4b and 4d correspond to a second channel and a fourth channel, wherein the first channel is composed substantially of channel portions 3a, 3d, 3e, 3f and 3i and the fourth channel is composed of channel portions 3g, 3j, 3k, 3l and 3c. The channel portions 3d and 3j and also 3l and 3f run parallel to one another; the channel portions 3k and 3f run in planes lying parallel to one another. In the third combination the pressure lines 4a and 4b in FIG. 1 and thus the first and second channel in FIGS. 2 and 3 are open. In this case, only a pressure present at the first inlet 4 is transferred by the channel structure 3 of the main body 2 to the outlets 6 and 7. In the fourth combination the pressure lines 4c and 4d in FIG. 1 and thus the third and fourth channel in FIGS. 2 and 3 are open. In this case, only a pressure present at the second inlet 5 is transferred by the channel structure 3 of the main body 2 to the outlets 6 and 7.

The valves 8 and 9 are cylindrical and have a solenoid 21a, 21b as well as a return spring 22a, 22b, by means of which a valve piston running inside the valve along the cylinder axis is movable. In the first switched position of the first valve 8 and second valve 9, in which the pressure lines 4a and 4c in FIG. 1 are open, the first valve 8 and the second valve 9 are not energized. The valve pistons are held here in the first switched position by the return springs. In the second position of the first and second valve 8 and 9, a current flows through the solenoids of the valves. The valve pistons are held in the second switched position by the force of the energized solenoids, overcoming the force of the return springs. The first and/or second valve may comprise a sensor 23a, 23b, for example a Hall sensor and/or an encoder, for measuring a piston position of the valve piston of the first and/or second valve.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A pneumatic system comprising:

a first and a second pneumatic unit; and a switching unit for interconnecting the first pneumatic unit and the second pneumatic unit, wherein the switching unit comprises:

a main body with a channel structure extending through the main body:

a first and a second inlet for introducing a pressure into the channel structure;

a first and a second outlet for discharging at least some of the pressure from the channel structure;

a first valve, wherein the first valve is switchable between a first switched position and a second switched position, the first inlet is in a pressure exchange connection with the first outlet via a first channel in the first switched position of the first valve, the second inlet being in a pressure exchange connection with the first outlet via a second channel in the second switched position of the first valve; and a second valve, wherein the second valve is switchable between a first switched position and a second switched position, the second inlet being in a pressure exchange connection with the second outlet via a third channel in the first switched position of the second valve, the first inlet being in a pressure exchange connection with the second outlet via a fourth channel in the second switched position of the second valve;

wherein the switching unit is operable to switch the first valve and the second valve independently from one another between a first switch configuration where the first valve is in the first switched position and the second valve is in the first switched position, and a second switch configuration where the first valve is in the first switched position and the second valve is in the second switched position;

wherein the first pneumatic unit has a first diaphragm fluid pump and a first drive device, and wherein the second pneumatic unit has a second diaphragm fluid pump and a second drive device, and wherein the first and/or the second drive device are designed to drive the first and/or the second diaphragm fluid pump.

2. The pneumatic system of claim 1, wherein the first valve is a 3/2-way valve or the second valve is a 3/2-way valve.

3. The pneumatic system of claim 1, wherein the first valve or the second valve is formed as a piston valve with a valve piston which is movable linearly inside the channel structure between the first and the second switched position.

4. The pneumatic system of claim 3, wherein the piston valve comprises a solenoid, wherein the valve piston is movable by an interaction with the solenoid.

5. The pneumatic system of claim 4, wherein the valve piston is movable from the first switched position into the second switched position by switching on an electrical current in the solenoid.

6. The pneumatic system of claim 4, wherein the piston valve has a return spring, by means of which the valve piston is movable from the second switched position into the first switched position if there is no current switched on in the solenoid.

7. The pneumatic system of claim 4, comprising a sensor for measuring a piston position of the valve piston.

8. The pneumatic system of claim 4, wherein the first valve comprises a Hall sensor or an encoder for measuring the piston position of the valve piston of the first valve.

9. The pneumatic system of claim 4, wherein the second valve comprises a Hall sensor or an encoder for measuring the piston position of the valve piston of the second valve.

10. The pneumatic system of claim 1, wherein the main body comprises a metal.

11. The pneumatic system of claim 10, wherein the metal is aluminum.

12. The pneumatic system of claim 1, wherein the first drive device is connected via a first inlet pressure line to the first inlet of the switching unit, the first diaphragm fluid pump is connected via a first outlet pressure line to the first outlet of the switching unit, the second drive device is connected via a second inlet pressure line to the second inlet of the switching unit, and the second diaphragm fluid pump is connected via a second outlet pressure line to the second outlet of the switching unit.

* * * * *